(12) United States Patent
Suzuki et al.

(10) Patent No.: US 6,540,853 B1
(45) Date of Patent: Apr. 1, 2003

(54) SUPER WATER-ABSORBENT COMPOSITE AND METHOD FOR PREPARATION THEREOF

(75) Inventors: Migaku Suzuki, Kanagawa (JP); Shingo Mori, Tokyo (JP)

(73) Assignees: Japan Absorbent Technology Institute, Tokyo (JP); Mitsubishi Corporation, Tokyo (JP)

( * ) Notice: Subject to any disclaimer, the term of this patent is extended or adjusted under 35 U.S.C. 154(b) by 0 days.

(21) Appl. No.: 09/744,063
(22) PCT Filed: Jul. 19, 1999
(86) PCT No.: PCT/JP99/03875
§ 371 (c)(1), (2), (4) Date: Jan. 18, 2001
(87) PCT Pub. No.: WO00/05444
PCT Pub. Date: Feb. 3, 2000

(30) Foreign Application Priority Data

Jul. 21, 1998 (JP) .......................................... 10-205280

(51) Int. Cl.[7] .............................................. D04H 1/00
(52) U.S. Cl. ...................... 156/62.2; 156/181; 156/279; 264/109; 264/122
(58) Field of Search ............................... 156/62.2, 181, 156/279; 264/109, 122

(56) References Cited

U.S. PATENT DOCUMENTS 6,403,857 B1 * 6/2002 Gross et al. ................ 604/365

FOREIGN PATENT DOCUMENTS

| JP | 7-268752 A | 10/1995 |
| JP | 7-279054 A | 10/1995 |
| JP | 8-41764 A | 2/1996 |

* cited by examiner

Primary Examiner—Sam Chuan Yao
(74) Attorney, Agent, or Firm—Pitney, Hardin, Kipp & Szuch LLP

(57) ABSTRACT

An absorbent composite sheet mainly consisting of a fibrous substrate web, a super absorbent polymer, and a bonding component bonding both of them with each other, wherein (a) the fibrous substrate web is a non-bonded web with a few of the constituent fibers bonded with each other, (b) a liquid mixture system is used of a medium mainly consisting of the super absorbent polymer and the bonding component, (c) a composite web is formed by adding the liquid mixture system to the fibrous substrate web, and (d) a liquid component is separated from the composite web so that fixing of the super absorbent polymer to the fibrous substrate web and bonding of the webs of the fibrous substrate web with one another are carried out at the same time. Methods of manufacturing such absorbent composite sheets are also provided.

28 Claims, 7 Drawing Sheets

IN-LINE MANUFACTURING PROCESS OF COATED MATERIAL USING CARD WEB

IN-LINE MANUFACTURING PROCESS OF COATED MATERIAL USING CARD WEB AND COTTON YARN

IN-LINE MANUFACTURING PROCESS OF COATED MATERIAL COMBINED WITH S.B. MANUFACTURING UNITS (BONDED WEB AND NON-BONDED WEB)

SUPER WATER-ABSORBENT COMPOSITE AND METHOD FOR PREPARATION THEREOF

FIELD OF ART

The present invention relates to methods of manufacturing super absorbent composite sheets wherein the making of a web into a non-woven fabric, the bonding of the web to a super absorbent polymer and the bonding of the particles of the super absorbent polymer with each other are all carried out effectively and little super absorbent polymer drops out in both wet and dry states. The present invention also relates to super absorbent composite sheets manufactured by any of such methods.

PRIOR ART

As an absorbent member for such absorbent article as a baby diaper, an adult incontinence diaper, a feminine hygiene product, a blood absorbent material and a mother's milk pad, the development of a highly absorbent sheet mainly consisting of a super absorbent resin polymer (SAP) and a wood pulp fluff the SAP being held in a thinner and more dimensionally stable non-woven fabric structure has been made energetically.

In order for a non-woven fabric to hold SAP, such methods as a method where a non-woven fabric having a structure preferable a substrate is prepared, the non-woven fabric is impregnated with acrylic acid monomer so that the monomer is polymerized a method where acrylic acid monomer is polymerized on a non-woven fabric, gelated non-cross-linked polymer is used to coat the non-woven fabric and cross-linking is then performed, a method where slurry of SAP dispersed in a medium is used to coat a non-woven fabric are applied.

First, there may be three fundamental properties required of a non-woven fabric substrate; (1) properties of a supporting member, (2) properties of holding and fixing SAP, and (3) properties to penetrate and disperse. In order for a non-woven fabric to hold SAP in its structure, the non-woven fabric needs to have a bulky structure having spaces among its constituent fibers and, if stated in extreme terms, the bulkier the non-woven fabric, the better the results. If such bulky non-woven fabric is supplied in a bulky wound-up roll from a non-woven fabric manufacturer, however, the transportation would be much costly and the amount of non-woven fabric wound up on roll would be greatly limited.

In such cases, it is conceivable to directly link a step of manufacturing a non-woven fabric to a step of having the non-woven fabric hold SAP, and there is an example in commercial practice of linking a step of manufacturing a thermally bonded non-woven fabric to a step of having the non-woven fabric hold SAP, which may be, however, complicated process-wise and costly initial-investment-wise.

Then, as an alternative a method of having the manufacture of a non-woven fabric and the holding of SAP carried out at the same time in a step of manufacturing a non-woven fabric may be thought of. As an example of such method, SAP in powder form is usually made to co-form with pulp or fiber as SAP is carried on an air stream. But dust may be generated or SAP powder moves inside an absorbent member, which is not desirable. Also, a so-called wet method is patented for; SAP is dispersed in a pulp slurry or a fiber slurry to form a sheet. Such method has a serious inherent limitation in that the fiber concentration is too low and the manufacturing cost becomes high.

In order to solve any such problems, a method should be adopted in which by having a component as a bonding agent co-exist with SAP in holding SAP so that the holding of SAP and the function of the bonding agent making a non-woven fabric are made to work at the same time. In general, a non-woven fabric is bulkiest when it is in an unbonded web and loses its bulkiness when it is finally made into a non-woven fabric.

SUMMARY OF THE INVENTION

The present invention makes it possible to manufacture a highly absorbent composite sheet having little SAP dropping out of it at both dry and wet states by a method in which an unbonded web in an original raw material condition is prepared, a liquid phase is formed in which a component is mixed to co-exist in the web to bond SAPs with each other and to function as a bonding agent to the web, the mixed liquid system is added to the web to stabilize it as a composite, and then liquid remaining in the web is removed, heat treated and then dried whereby the web is made into a non-woven fabric, the web is bonded with the SAP and the bonding of the SAPs is completed.

That is to say, the present invention relates to a method for manufacturing a highly absorbent composite sheet mainly consisting of a fibrous substrate web, a super absorbent polymer resin and a component to bond the resin and the substrate, wherein (a) said fibrous substrate web is a-yet-to-be-bonded web having little constituent fibers bonded with each other, (b) a liquid mixture system mainly consisting of a medium containing said highly absorbent polymer resin and said bonding agent, (c) a composite web is formed by adding said liquid mixture system to said fibrous substrate web, and (d) liquid component remaining in the composite web is removed whereby said highly absorbent polymer resin is made to be fixed to said fibrous substrate web and the webs comprising said fibrous substrate web are bonded with each other at the same time.

In the present invention, a preferable unbonded web may be a carded web or a laminated carded web and a carrier for guide may be used together with the carded web.

An unbonded web as obtained at dry state may be pretreated by means of a pretreatment liquid consisting of water or a medium miscible with water.

Also, an yet-to-be-bonded web may be an aqueous web to be obtained by a wet formation method or its laminate. Such unbonded web may be obtained by preliminarily treating a carded web or a wet formed web under a high pressure water stream.

The fiber component comprising an unbonded web is preferably a combination of easy-to-thermally-fuse fibers and synthetic fibers, and the fiber component is preferably finer than 2d composed of a first fiber layer mainly consisting of finer than 10d hydrophobic synthetic fibers and a second fiber layer mainly consisting of finer than 3d hydrophilic fibers.

A yet-to-be-bonded web may be formed from opened fibers of a wood pulp and easy-to-be-thermally-fuse fibers of 20 mm or shorter.

In the present invention, as examples of a liquid mixture system, such systems may be applied as a system where in a 1% or less melted solution of polyethylene oxide having a molecular weight of 100,000 or more particulate highly absorbent resin is dispersed to make a slurry, a system where in an aqueous emulsion of an ethylene-vinyl acetate copolymer a particulate highly absorbent resin is dispersed to make a slurry, a system where in an aqueous slurry of a highly absorbent resin containing a solvent system to be obtained by negative phase suspension polymerization and an aggregated gel of a highly absorbent resin to be obtained by aqueous solution polymerization are diluted in polypropylene glycol to make an easy-to-flow mixture, and a system where in an aqueous dispersion liquid of microfibrillated fibrils having a hydrating property a particulate highly absorbent resin is dispersed to make a slurry.

To this liquid mixture system, microfibrillated fibrils having a hydrating property may be added.

Furthermore, to said pretreatment liquid, microfibrillated fibrils having a hydrating property may be added.

In the present invention, a highly absorbent resin is preferably the one cross-linked on the surface so that it is 0.9% saline and has an AUL (absorbance under load) of 25 ml/g or higher under 20 g/cm$^2$.

As other specific examples of a highly absorbent resin, an amino acid type polymer having a main component of aspartic acid and a polyacrylic acid type polymer with surface cross-linking omitted are listed.

Microfibrillated fibrils having a hydrating property are specifically microfibrillated cellulose or bacteria cellulose consisting of cellulose.

The micro fibrillated fibril cellulose fibers may be used as such systems as a system where the fibril cellulose fibers are uniformly dispersed at 1.5% to 0.2% concentration in a mixed medium of water and propylene glycol and particulate highly absorbent resin is dispersed at 5% to 50% concentration in the dispersion liquid to make a slurry, a system where the fibril cellulose fibers are uniformly dispersed at 1.5% to 0.2% concentration in a mixed medium of water and ethylene alcohol and particulate highly absorbent resin is dispersed at 5% to 50% concentration in the dispersion liquid to make a slurry, and a system where the fibril cellulose fibers are uniformly dispersed at 1.5% to 0.2% concentration in a three component mixed medium of water, ethanol and propylene glycol and particulate highly absorbent resin is dispersed at 5% to 50% concentration in the dispersion liquid to make a slurry.

A highly absorbent composite sheet according to the present invention is preferably a highly absorbent composite sheet consisting of an unbonded web (A), said highly absorbent resin (B) and said bonding component (C), wherein the percentage of said highly absorbent resin (B) is 50% or more satisfying the following formula:

$$B/(A+B+C) \times 100 \geq 50$$

More preferably, a highly absorbent composite sheet according to the present invention is a highly absorbent composite sheet consisting of an unbonded web (A), said highly absorbent resin (B) and said bonding component (C), wherein the percentage of said highly absorbent resin (B) in the total of said highly absorbent resin (B) and said bonding component except for said yet-to-be-bonded web which are absorbance contributing components is 70% or more satisfying the following formula:

$$B/(B+C) \times 100 \geq 70$$

Figure 1:
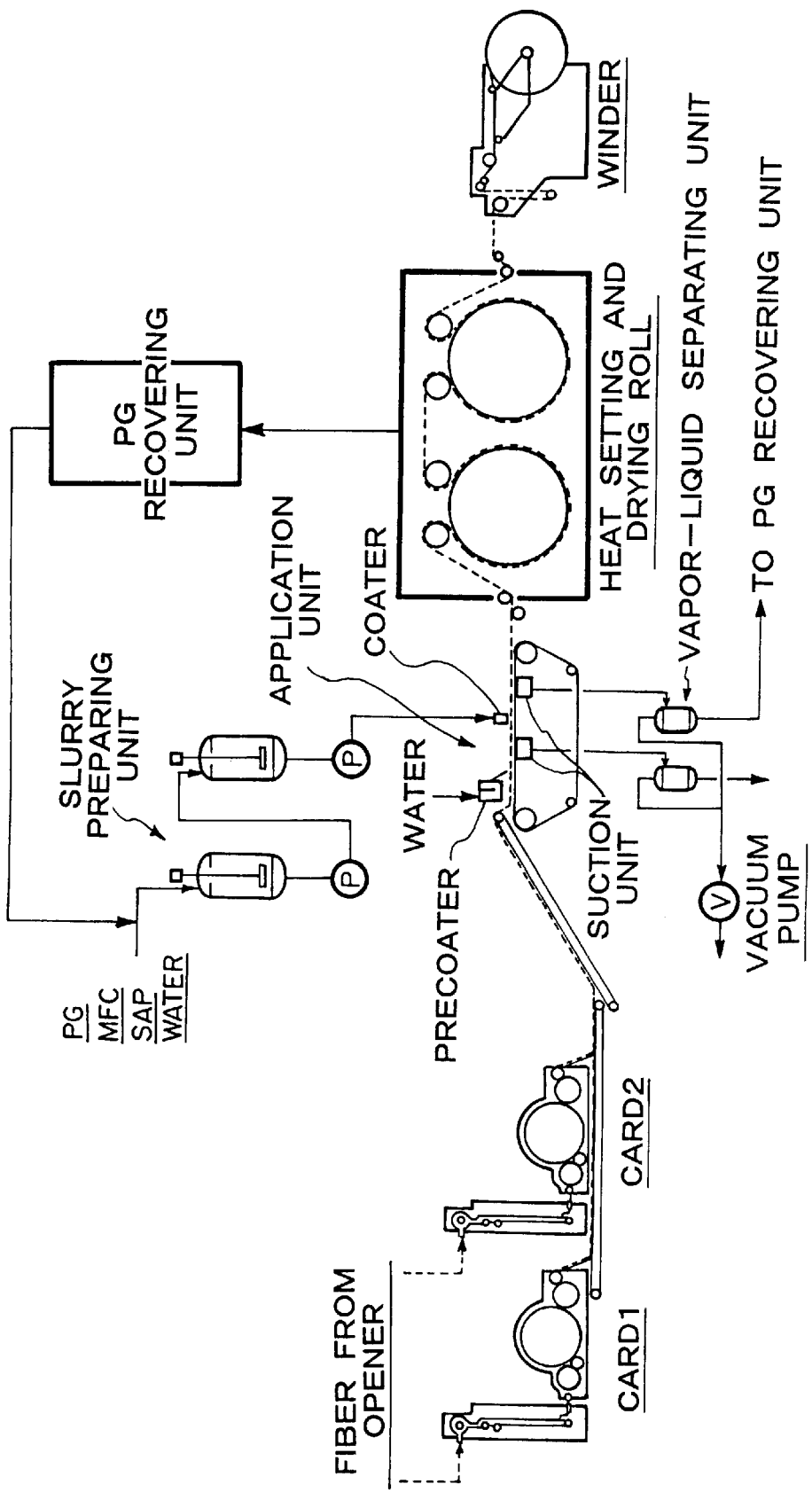
FIG. 1 is a schematic diagram showing a first manufacturing process based on a method of manufacturing a highly absorbent composite according to the present invention.

BEST MODES OF EMBODYING THE INVENTION (Manufacturing of Unbonded Web)

In the present invention, a non-woven fabric is bonded by means of a bonding agent which co-exists with SAP, so that if a web is manufactured it is sufficient for the manufacturing of a non-woven fabric; that is to say, such steps of bonding, drying and heat treating of a non-woven fabric are not required. The web can be used whether it is dry or wet if manufactured by a wet method.

It is very important how bulky such unbonded web is prepared, and its strength is sufficient if it does not break when transported in roll or net. For example, a carded web of synthetic fiber, an air formation mat of synthetic fiber and a wet formation mat of short cut synthetic fiber and pulp are good for such unbonded web. A wet formation method in general cannot impart bulkiness to a web so that for the present invention, such specialized methods as the addition of hydrophobic synthetic fiber and the making of a foamed paper like product are preferable.

To make a non-woven fabric as bulky as possible, however, it would not be sufficient only if it is left unbonded, and various means are adopted for making such unbonded web bulkier. One of such means is to use a coarse denier hydrophobic fiber having high resilience or a composite fiber having a crimpability mainly as a constituent fiber element. For example, polyester fiber of 5 denier or coarser, a coarse and hollow polyester fiber developed for wadding of "futon" comforter or a conjugate fiber of polyethylene and polyester are good candidates.

These so-called hibulk and highly resilient fibers, however,:

(1) do not have a self-holding property of web and are too weak for handling; and (2) are lacking in such capability of absorbing and dispersing liquid as required of a substrate for holding SAP.

These drawbacks of such hibulk and highly resilient fibers pose very important problems. Solutions of such problems are a method of feeding the bulky web on a carrier sheet, a method of making and using a carrier sheet of a thin non-woven fabric of more or less than 10 to 15 g/m$^2$ made into hydrophilic SM or SMS, a method of making and using a carrier where-cotton or spun rayon yarns are arranged, and a method of making and using a carrier where relatively hydrophilic and length-wise strong rayon spun laces are arranged in tapes. The most practical and secure method is to preliminarily treat in a low pressure water jet (hereinafter called "WJ") of 20 to 30 kg/cm², for the purpose of pre-needling, a multilayer web of a bulky synthetic fiber web and a thin rayon web as folded on each other. By this method the bulky synthetic fiber web is never entangled in the WJ and keeps its bulkiness while the rayon web layer only is lightly entangled to function as a future penetrating and dispersing layer and at the same time plays the role of a carrier sheet when a bulky web is manufactured. A web layer treated in the WJ does not dry and is, as it is wet, guided into a next step of holding SAP.

As well understood from the foregoing, the term "unbonded web" used in the present invention means a web with the bonding of its constituent fibers with each other not yet completed. That is to say, a web whose strength, thickness and surface condition when an unbonded web is made into a "bonded web" where its constituent fibers are bonded with each other through a non-woven fabric making process have not yet been realized is meant by the term "unbonded web". If one attempts to define it in numerical values, when the tensile strength (P1) and the thickness (T1) of an "unbonded web" are compared with the tensile strength (P2) and the thickness (T2) of a "bonded web" which has passed through a usual non-woven fabric making process, P1/P2 is 0.5 or lower and T1/T2 is 1.2 or higher. For example, in the case of an unbonded web containing easy-to-thermally-fuse fibers to be bonded by a thermal bond, on average P1/P2 was 0.2 or lower and T1/T2 was 1.5 or higher. In addition, in case a water jet entangling of a carded web is applied, when a web only pretreated in water steam entangling is compared with a web completely treated in entangling, on average P1/P2 was 0.4 or lower and T1/T2 was 1.3 or higher.

If another definition is applied, a liquid mixture system containing a super absorbent polymer resin and a bonding agent is added to an "unbonded web" to make a composite and then drying and heat treatment are applied so that a "highly absorbent composite sheet" is obtained. If the tensile strength (P1) and the thickness (T1) of the "unbonded web" are compared with the tensile strength (P3) and the thickness (T3) of the "highly absorbent composite sheet", P3/P1 is on average 3.0 or higher and preferably is 5.0 or higher, while, in the comparison of T1 and T3, since the super absorbent resin is compressed as surrounded by the spaces made by the fibers in spite of the weight being more than doubled by being made into a composite, T1>T3. Preferably, T1>T3.

The thicknesses are measured in the present invention as follows: in case of an unbonded web, since it is susceptible to loading, 100 cm² or larger samples are folded in at least five layers to make a sample for thickness measuring and pressurizing is applied on the entire area of the sample and that under 3 g/cm².

(Preparation of Liquid Mixture System)

A super absorbent resin to be added to an unbonded web to make a composite as described above and a liquid mixture system containing a bonding agent for bonding the resin and the web are explained below:

First of all, a liquid mixture system is a concept including solution, slurry, sol and fluid gel states. Examples to be used in the present invention being shown, a first group is a method of uniformly dispersing a super absorbent resin in an organic solvent solution of a polymer having a capability of bonding. For example, if a super absorbent resin is dispersed in a solvent such as an acetone solution of cellulose acetate or an amine oxide solution of cellulose as shown in Patent Publication Hei 9-299399, an alcohol solution of hydroxypropyl cellulose as shown in Patent Publication Sho 60-217241, or polyethylene oxide solution dissolved in an organic solvent such as acetonitrile as shown in Patent Publication Hei 1-182362, the super absorbent resin is dispersed uniformly without swollen and is formed into a stable slurry without being coagulated by the high viscosity of the solution. A polymer solution functions satisfactorily as a binder of a super absorbent resin or an unbonded web, but, in case a bonding agent component is used to cover the whole of the super absorbent resin like a film in an obtained highly absorbent composite sheet, may impede the rate of penetration of liquid to be absorbed. In such case, such means needs to be applied as adding inorganic powder to the liquid mixture system or making it foamed. Among other examples of using organic solvents is a method of dispersing super absorbent resin powder into an organic solvent emulsion of a rubber type binder usually used as a base of coating. Among the first group, a preferred method is to disperse super absorbent resin in a diluted solvent of polyethylene oxide (PEO) of a high degree of polymerization of 100,000 or higher and 5,000,000 or lower because in that method the penetration is relatively good. The concentration of PEO in the diluted solution is 1% or lower and preferably 0.1 to 0.5%.

Among the second group is a method of dispersing super absorbent resin in an aqueous solution of a polymer having a bonding property. For example, there are a method of dispersing super absorbent resin in a viscous aqueous solution of P. V. C., CMC, polyvinyl pyrrolidone, acrylamide or polyethylene oxide or a method of dispersing super absorbent resin in an aqueous emulsion very often used as an emulsion binder for non-woven fabrics such as an ethylene-vinyl acetate copolymer or an aqueous dispersion of polyethylene. In either of these methods, since the super absorbent resin becomes easier to gelate in water, a swelling inhibitor needs to be added to co-exist with the liquid mixture system, for example, a small amount of an inorganic salt being added or a water soluble organic solvent being added, so that the swelling may be controlled and the emulsion does not coagulate to break down. Among the second group, a method of adding super absorbent resin powder to a system in which propylene glycol is added to an aqueous emulsion of ethylene-vinyl acetate copolymer containing a relatively high content of vinyl acetate such as Everflex (Mitsui Chemical Co., Ltd.) and Sumikaflex (Sumitomo Chemical Co., Ltd.) is a preferable method.

As a third group of methods, a method of dispersing super absorbent resin to make a slurry in an aqueous dispersion liquid of microfibrillated fibrils having a hydrating property or a mixture solvent of water and a water soluble organic solvent is a preferred method.

In the present invention, a network structure of holding SAP particles in position is composed of so-called microfibrillated fibrils. This network functions to prevent SAP particles from coagulating with each other when a highly absorbent composite sheet is manufactured to stabilize and to make uniform the dispersion condition and at the same time to serve as a binder to bond SAPs with each other and SAPs with a supporting sheet.

These microfibrillated fibrils are very fine in general having an average diameter of 2.0 $\mu$m to 0.01 $\mu$m with a mean value of 0.1 $\mu$m or finer, and have a sufficient water resistance to prevent the structure of a highly absorbent composite sheet from breaking down immediately when SAP absorbs water to swell, without holding back the water perviousness and the swelling of SAP. It is to be particularly noted here that the microfibrillated fibrils have an extremely strong hydrating property to bond with water as a solvation, and that by virtue of such strong hydrating property when the fibrils are dispersed in an aqueous medium, they hydrate with water to give a high viscosity and keep stably the dispersed condition. The hydrating property is measured in terms of the amount of water contained when the fibrils as dispersed in water are centrifuged at 2000 G for 10 min and the preferable hydrating property is expressed in terms of the amount of water of 200% or higher as measured by tappi of 20 ml/g or more.

In this specification the term "microfibrillated fibrils" is used to mean collectively fibrous materials exhibiting a strong hydrating property and in some cases those having an average diameter of 2.0 µm or coarser and even a mixture of fibrils with microfibrils.

Also, the components constituting the fibrils are in general cellulosic, but may be fibrillated polyethylene, polypropylene, ethylene-vinyl acetate copolymer and co-fibrils of any such synthetic polymer with cellulose. These fibrils may be prepared by any method described in Examined Patent Publication Sho 49-1245.

Cellulosic microfibrillated fibrils preferable for the present invention may be obtained by microfibrillating cellulose or any cellulose derivative. For example, such fibrils may be obtained by grinding down by friction and finely opening by beating wood pulp. Such microfibrils are called "MFC (microfibrillated cellulose)" and, if further microfibrillated, "S-MFC (super microfibrillated cellulose)".

Also, such fibrils may be obtained by grinding by friction and finely opening by beating short cut staples of man-made cellulose fibers (Polynosic, Bemberg, or solvent spun Lyocel).

Furthermore, microfibrillated fibrils may also be obtained through the metabolism of mticroorganism. In general, a so-called acetic acid bacterium such as Acetobactor Xylinum is cultured by agitation in a medium containing an appropriate carbon source to produce crude microfibrils which microfibrils are then refined. These microfibrillated fibrils are called "BC (bacteria cellulose)".

Also, so-called fibril-like material to be obtained by coagulating tinder shearing stress a copper ammonia solution of spinnable cellulose, an amine oxide solution, a cellulose xanthate aqueous solution, or an acetone solution of diacetyl cellulose is further dissociated to obtain a microfibril-like material which material may be used for the present invention.

Details of these microfibrillated fibrils are described in Patent Publication Sho 48-6641 and Patent Publication Sho 50-38720 and such fibrils are available on the market under the trademarks "Celcream" (manufactured by Asahi Chemical Industry Co., Ltd.) and "Celish" (manufactured by Daicel Chemical Industries, Ltd.).

Particularly suitable for the present invention are MFC, S-MFC and BC. The details of S-MFC are described in Examined Patent Publication Hei 8-284090 and Unexamined Patent Publication Hei 5-80484.

The uses of MFC and S-MFC as collectively called "MFC" are explained in more detail below. Such MFC whose solid content is concentrated up to as high as 30% is available on the market, and such MFC needs a step of dilution and dissociation so that it costs labor on top of the concentration cost required. For the present invention such MFC as has higher water content and a solid content of 10% or lower is more preferable. However, if the solid content is made down to 2% or lower, the water content gets too much and the range of selecting the content of MFC in a mixture system of an organic solvent and water becomes narrow. In case such MFC as is so low in the solid content is used, it is recommended that microfibrillation is performed not in a single water system, but in an organic solvent/water system prepared to contain an organic solvent in making microfibrillete fibrils of raw material pulp whereby an MFC dispersion liquid of around 2% dilution as may be obtained on the market can be used for the present invention.

The uses of BC are also explained in detail. Since BC is obtained as a metabolism product of bacterium, the concentration and the form of BC depend on the manners of culturing and of harvesting. In order to make it uniform, BC after harvested and refined as diluted down to 2% or lower needs to be dissociated by means of a mixer or a defibrator whereby clusters of fibrils in coagulation are made further finer and more uniform and thus becomes much high in viscosity providing a better binder for SAP. Such BC undergoing such dissociation treatment is more suitable for the present invention.

To prepare a mixture system of microfibrillated fibrils as represented by MFC and of a Super absorbent resin, first of all, a mixture liquid of water and an organic solvent is prepared and in the liquid MFC is dispersed to make a dispersion liquid of 2% to 1% MFC. Then, a super absorbent resin is dispersed in the MFC dispersion liquid to make a slurry. This is a generally applied method of preparing a slurry. An organic solvent to be used for the method is selected from such solvents as are soluble in water function to prevent a super absorbent resin from coagulating and controls the swelling of the resin. Its representative composition is glycol/water=70/30 or ethanol/water=60/40. The dispersion concentration of a super absorbent resin is preferably 10% to 50%.

As a fourth group, there is a method of having a super absorbent resin, as in sol or gel to be obtained in making the resin, play the dual roles of bonding an unbonded web and serving as an absorbent component utilizing the viscosity which it may have before it is dehydrated and any remaining solvent is removed. This method may be further divided into two submethods: one of utilizing an aqueous gel to be obtained after negative phase suspension polymerization and the other one of utilizing an aqueous gel after polymerization of an aqueous solution.

A: Utilization of Aqueous Gel After Negative Phase Suspension Polymerization

For example, acrylic acid is added to a solution in which sorbitan monostearate is added to and solved in cyclohexane, which is then neutralized with NaOH. A solvent and a chain transfer agent are then added and the system is heated to perform radical polymerization under agitation to obtain an aqueous polymer liquid containing the solvent in suspension. This suspension liquid contains an aqueous polymer of more or less 30% concentration and the water content of the aqueous polymer is approximately 60%. This suspension liquid is added to an unbonded web, which is then made to pass through a vacuum zone to remove any remaining solvent and water to obtain an absorbent composite sheet. The absorbent composite sheet as thus obtained can be used in some applications, however, the bonding of SAPs with each other and with the web turned out to be insufficient. Then, an aqueous dispersion liquid of 1% MFC as microfibrillated fibrils is added to the suspension liquid after the polymerization reaction in a way that the added MFC was 2 to 10% against the polymer, so that the dispersion liquid well mixes with the aqueous resin slurry stably to form a viscous slurry. The unbonded web is spray-coated with this slurry containing MFC, and when dried after suction operation and removal of solvent by pressing, an absorbent composite sheet in which the polymers are strongly bonded with each other and with the web is obtained.

In adding MFC, it may be added in an aqueous dispersion or co-existed with polypropylene glycol or ethanol.

B. Utilization of Aqueous Gel After Aqueous Solution Polymerization

For example, to a reaction liquid in which to 30% aqueous solution of acrylic acid (neutralization rate 75%) polyethylene glycol diacrylate is added as a cross-linking agent, a redox type catalyst system of sodium persulfate/L-ascorbic acid is added to run polymerization so that an aggregated aqueous gel is obtained. This gel has a water content of 70% or so, and as such is difficult to handle for it is gelated as a whole, so if propylene glycol of 0.5 to 2.0 times as much as the gel is added to the gel and the gel is agitated, it is made to change into a fluid viscous gel. This gel can be extruded into film-like form by means of a pressurized extruder or the like. The film-like product is then added to the above-mentioned unbonded web so that an integrated composite condition is obtained after vacuum removing of any remaining liquid and compressing operations. Then, the composite in such condition is made to undergo the steps of dehydrating, removing of remaining solvent and drying so that an absorbent composite sheet is obtained. This sheet as it is thus obtained, however, is observed to have a drawback of insufficient bonding capability. If the surface strength of such sheet is measured by a scotch tape test, it is seen that super absorbent resin drops off and the bonding of SAPs with each other and with the web is insufficient. In addition, the result of an absorbance test shows that the surface of such sheet becomes filmy and the rate of absorbance is low.

With that, to the gel after the above-mentioned polymerization a dispersion liquid in which 1.5% of MFC is dispersed in a mixture solvent of propylene glycol 80% and water 20% is added in the ratio of MFC being 2% to 10% against the gel and the agitation is run in a kneader, so that the gel is made to change into a fluid viscous gel. This gel is further diluted to make a slurry-like product, which can easily be transferred by a slurry pump just like a common slurry.

Then, such slurry to be obtained by adding a dispersion liquid containing MFC of two times as much as the aggregated gel is added to the unbonded web by means of a slurry pump in slit lines. After the vacuum removing of any remaining liquid and compressing, an integrated composite is obtained and then after dehydrating by hot air and removing of any remaining solvent, an absorbent composite sheet is obtained. When a scotch tape test is applied on the absorbent composite sheet, it is observed that the SAPs are bonded with each other and the SAP is bonded with the web strongly enough so that very little super absorbent resin peels off.

As such gel after the polymerization, as proposed in Unexamined Patent Publication Hei 10-120818, a gel containing air bubbles of water content of 30% to 90% to be obtained by having a foaming agent in co-existence when the polymerization reaction is run may be used in order to improve the absorbance and permeability. In this case, too, the absorbance can be much improved by having the above-mentioned microfibrillated fibrils in co-existence in a polyvalent alcohol as a plasticizer. (SAP (super absorbent polymer) to be used and its form of use)

Super absorbent polymer generally abbreviated as SAP is in general a carboxymethyl cellulose, polyacrylic acid and its salts, a cross-linked acrylate polymer, starch-acrylic acid grafted copolymer, a hydrolysis product of starch-acrylonitrile grafted copolymer, a cross-linked polyoxyethylene, a cross-linked carboxymethyl cellulose, polyethylene oxide, a partially cross-linked water swellable polymer such as polyacrylamide, or a isobutylene-maleic acid copolymer. By drying any such polymer, base polymer particles are obtained. Next, in general an after treatment of the surface of such polymer is run to improve the cross-linking density and at the same time an anti-blocking agent is added to control the blocking propensity caused by the absorbing of product particles.

Also, a biodegradable amino acid cross-linked polymer or a super absorbent polymer of bacterium source, a cultured product from Alcaligenes Latus, may also be used. SAPs may be in the various forms of particles, granules, film, sols, suspension, gels or non-woven fabrics. Any of these SAPs may be used for the present invention. Those SAPs which are preferable for the present invention are such SAPs in the forms of particles, granules, flake, pellets or short needles as are uniformly dispersable in a dispersing medium. These SAPs are herein called "particles or particulate".

In general, the SAP whose surface is cross-linked is high in AUL value (absorbance under load); specifically, it has an AUL of at least 20 ml/g under the load of 20 $g/cm^2$ and in general an AUL of 25 ml/g or higher under such load. Such SAPs have a wide selection of dispersion mediums so that they can be uniformly dispersed in mixture mediums of organic solvents and water among organic mediums.

On the other hand, however, such SAPs as are not surface cross-linked or difficult to surface cross-link have a narrow selection of dispersion mediums, and they need to be dispersed in a hydrophobic medium such as cyclohexane using a surfactant or in a three component system such as propylene glycol/ethanol/water under selected appropriate conditions.

In the present invention, to have an effective binding agent for the purposes of binding SAPs with each other and SAP with a web, the surface treatment of the SAP needs to be limited to as much as surface cross-linking. For example, the surface treatment using an anti-blocking agent or an anti-caking agent should not be applied for such surface treatment may impede the bonding effects.

(Application of Liquid Mixture System to Unbonded Web)

There are various means of applying a liquid mixture system to an unbonded web, i.e. adding and making a composite of the web, which means will be explained later. Here particularly important is a pretreatment of an unbonded web.

An unbonded web to be used in the present invention may obtained by a variety of methods, as describe in the above, and any such web is very bulky with an apparent specific gravity, as calculated from the thickness obtained under 3 $g/cm^2$, of at least 0.1 $g/cm^2$ or lower or preferably 0.08 $g/cm^2$ to 0.005 $g/cm^2$ and has dents and has a rugged surface very much susceptible to change if pressing or the like, so that it needs to be transferred to the process of applying a liquid mixture system to the web on a carrier sheet or a belt conveyor without being pressed by a roll. The web being on such carrier sheet or a belt conveyor tends to be more uneven or non-uniform for air dwells on the carrier sheet or the belt and that there may be formed spaces between the web and the sheet or belt, so some or other means needs to be applied to have the web well fit onto the sheet or belt.

In addition, as described later, in case a liquid mixture system is applied to a web by means of a coater, being a contact type, the coating tends to be non-uniform, so that a pretreatment to make the surface of the web uniform or a substrate smooth is needed. Also, since a web being bulky means that it is porous, too, in case a relatively large slurry is applied by means of a curtain coat and a vacuum zone is provided under the coat, a liquid mixture as applied may leak down passing through a porous unbonded web. In such case, any voids formed need to be filled by means of a pretreatment before a liquid mixture system is applied. In handling an unbonded web containing a fibrous material having a hydrophobic or water repellent property, the liquid mixture tends to poorly fit onto the web and delamination may take place, and in such case a pretreatment is preferably needed to make the web hydrophilic.

For the reasons given above, in practicing the present invention, it is preferable that, only after an unbonded web is pretreated, a liquid mixture system is applied. As a typical method of doing so, there is a method of preliminarily saturating a web in a component as a medium of a liquid mixture system. i.e. in water if it is of an aqueous system or in a mixture medium if it is of a mixture system. In general, water or such mixture medium is added by means of a flow coater, and after an excessive part of water is made to drop down to be removed, a web is guided to a process of applying a liquid mixture system to the web, whereby the surface is made smooth and thus well slithery, dents on the surface are filled and air partially dwelling is made to go out. Such process is herein called a more generic term "precoat treatment". For this precoat treatment, water or an aqueous medium solution is preferably used or the above-mentioned microfibrillated fibrils may be dispersed to co-exist in such water or aqueous medium solution. Note that this precoat treament can be omitted for a web in a wet condition obtained through a wet formation method or a water entangling treatment.

To thus precoat treated unbonded web, a liquid mixture system is added to make a composite of it in a contact or a non-contact way. The patterns of adding and making a composite may be in the various forms of dots, lines, whole area, and sea islands. An application device suitable for each of such forms is selected. Application systems may be, typically for example, impregnation, coating with such device as a roll coater, a knife coater, a transfer coater, an extrusion coater, a kiss coater or a curtain coater, nozzle extrusion, an extrusion into film or spraying.

A liquid mixture system as is applied to an unbonded web is made integrated with the unbonded web passing through a vacuum zone and a pressurizing zone. Excess water and solvent which were contained in the web are removed in the vacuum zone and the pressurizing zone as recovered liquids and at the same time a structure in which a super absorbent resin component together with a bonding component are contained in the spaces of fibers comprising the web is formed.

A composite made integrated by the pressuring is made then to pass through a drying and a heat treatment step in which any residual water and solvent are removed and at the same time the structure is fixed. In the drying and heat treatment steps a thermal fusion is made to progress and at the same time the web is made into a non-woven fabric in case the unbonded web contains thermally fusible fibers, which is an important feature of the present invention.

The processes of manufacturing highly absorbent composite sheets according to the present invention are explained below with reference to the drawings showing the specific configurations of the devices therefor.
(In Line Manufacturing Process of Coating Substrates Based on Carded Web)

FIG. 1 shows an example of a process of manufacturing a non-woven fabric substrate, in which a carded web line is incorporated, wherein a manufacturing process of a highly absorbent composite sheet according to the present invention is embodied. In FIG. 1, fibers sent from an opener are processed into a carded web on a card and sent to an application unit on a conveyor. An example of the composition of a carded web consists of:

Top layer: PET (5d)/bicomponent fibers (2d), 20 g/m$^2$, and

Bottom layer: rayon (1.5d)/bicomponent fibers (2d), 20 g/m$^2$

The application unit functions in a step of moving a carded web along a planate treatment region structured on an endless belt to coat the carded web with water from a precoater and then with a slurry from a coater.

The slurry fed from the coater, as used in this example, is prepared by mixing and agitating polyethylene glycol (PG), microfibrillated fibrils (MFC), a super absorbent resin polymer (SAP) and water in a slurry manufacturing unit. This slurry is formed into a coating of a desired thickness as liquids contained in the slurry are removed while it is made to move through the treatment region.

In the treatment region, to the carded web water is fed from the precoater and the slurry is fed from the coater, and then in order to remove any excessive water and solvent from the carded web, a suction unit is provided on the bottom surface of the endless belt in the treatment region. Each suction unit serves to remove by suction any excessive liquids from the carded web on the endless belt by means of a vacuum pump via a gas-liquid separation unit. Such liquids removed by suction undergo a gas-liquid separation in the gas-liquid separation unit, and the liquid component, which contains much propylene glycol, coming from a suction unit provided after the coater is recovered at a propylene glycol recovery unit after only the liquid is separated at the gas-liquid separation unit, which propylene glycol is reused at the slurry manufacturing unit.

The carded web coated at the application unit is heat treated and dried as it is made to pass through on the surfaces of heat treatment and drying rolls in succession and finally wound up on a roll at a winder.

This manufacturing process performs the making of an unbonded web into a non-woven fabric and the fixing of super absorbent resin particles on the non-woven fabric at the same time.
(Manufacturing in Line of Coating Substrate in Combination of Carded Web and SB)

Figure 2:
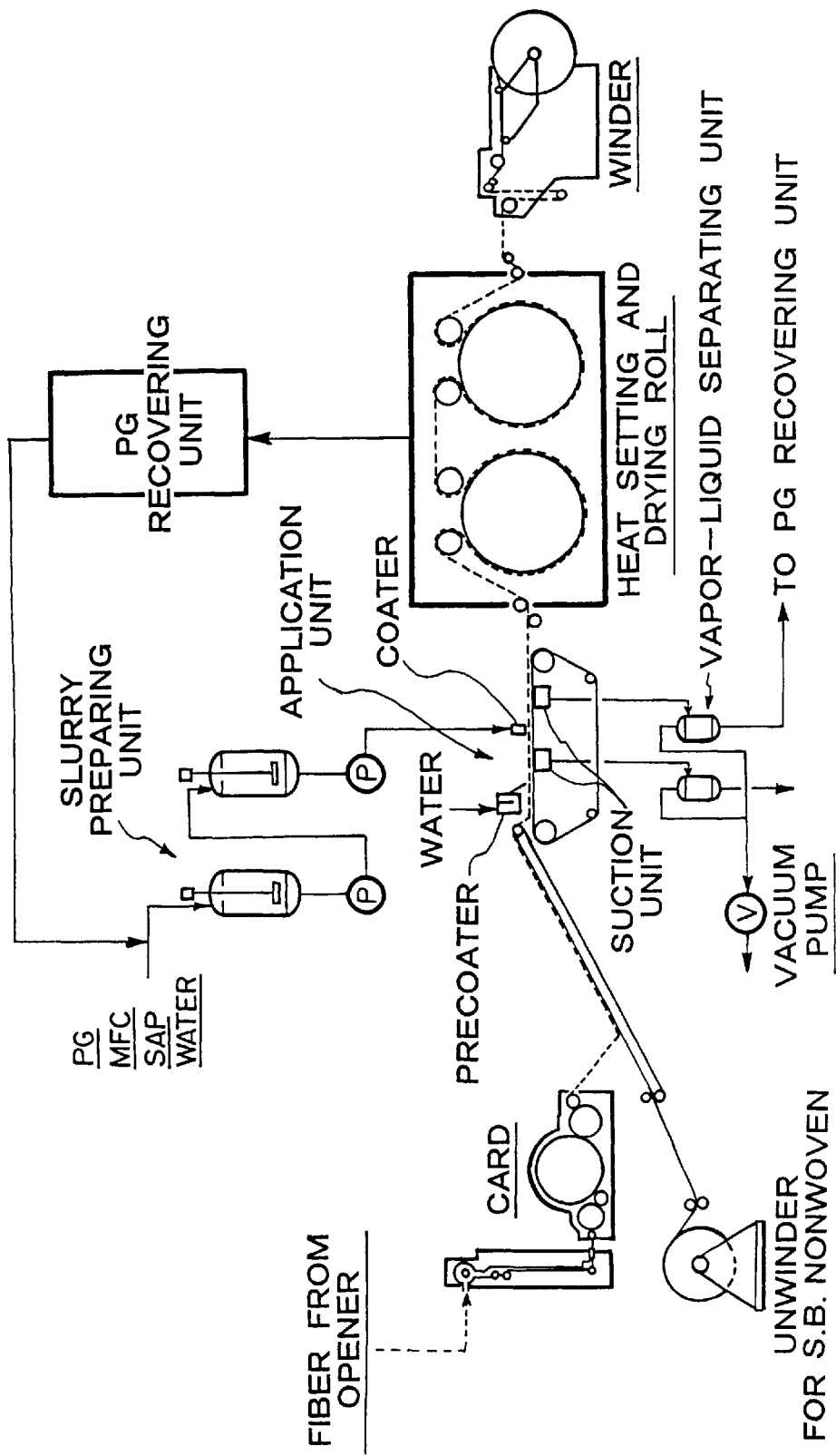
FIG. 2 is a schematic diagram showing a second manufacturing process based on a method of manufacturing a highly absorbent composite according to the present invention.

In the manufacturing process shown in FIG. 2, a spun-bonded non-woven fabric (SB) is drawn from an SB unwinder, and on the SB a carded web is laminated as it is led to an application unit via a conveyor and then the SB as it is laminated is led to the application unit. The spun-bonded non-woven fabric is a carrier for the carded web which is laminated on the non-woven fabric, and by means of the carrier the unbonded web which is not sufficiently strong can be transferred stably. Any other configuration and operations are the same as those of the manufacturing process of FIG. 1, so that detailed explanation is omitted.

A preferable example of the composition of the carded web is PET (5d)/rayon (1.5d)/bicomponent fibers (2d), 20 g/m$^2$.
(Manufacturing in Line of Coating Substrate in Combination of Carded Web and Cotton Yarns)

Figure 3:
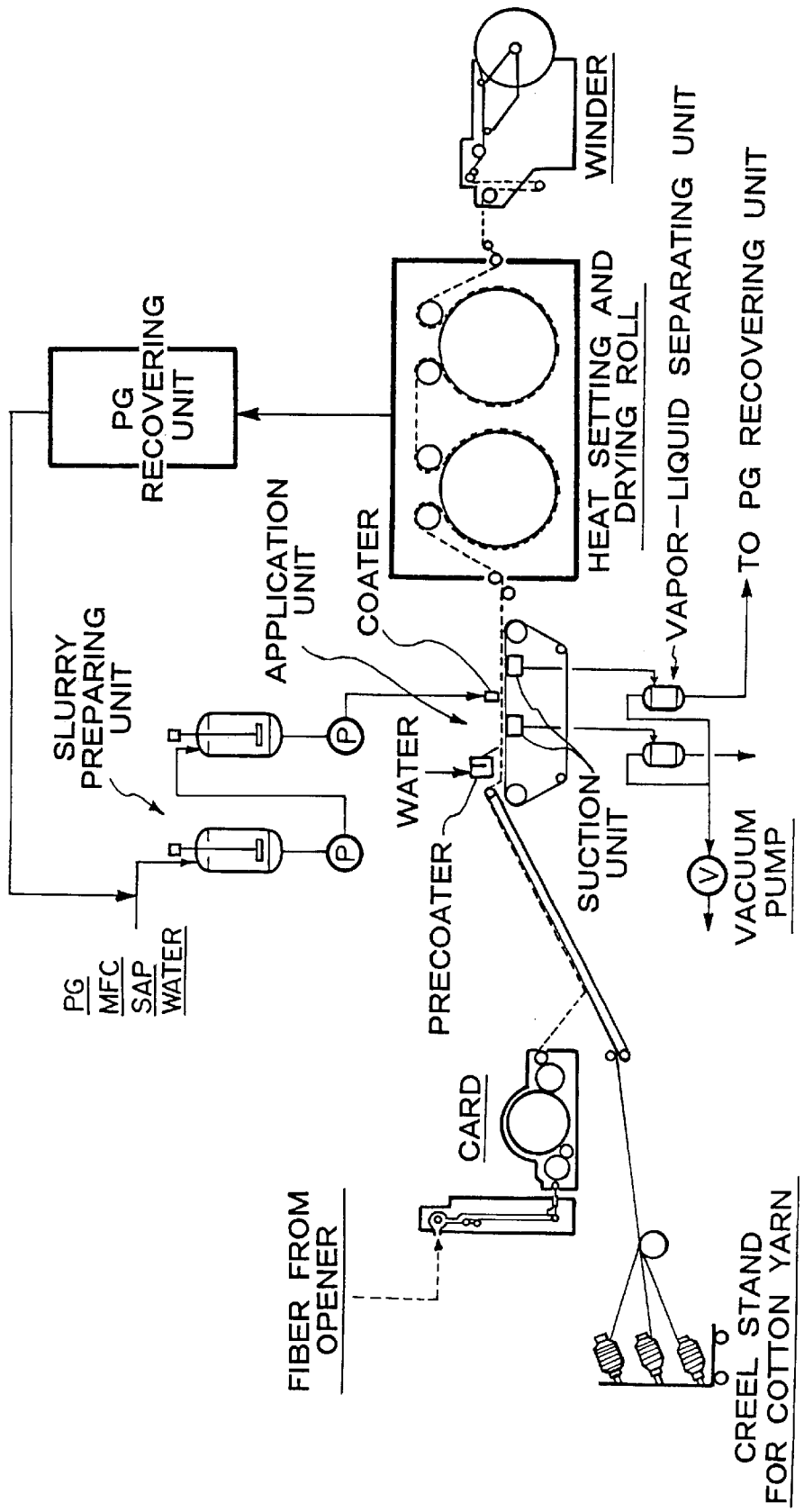
FIG. 3 is a schematic diagram showing a third manufacturing process based on a method of manufacturing a highly absorbent composite according to the present invention.

In the manufacturing process shown in FIG. 3, many cotton yarns (spun cotton yarns) are as a carrier drawn from a cotton yarn creel stand in parallel at appropriate intervals of, for example, 5 mm, and on the cotton yarns a carded web from a card is laminated as the yarns are led to an application unit via a conveyor and then the cotton yarns as they are laminated are led to the application unit. Any other configuration and operations are the same as those of the manufacturing process of FIG. 1.

A preferable example of the composition of the carded web is PET (5d)/rayon (1.5d)/bicomponent fibers (2d), 20 g/m².

It is noted that, instead of the cotton yarns as the carrier, spun-laced non-woven fabric as slitted into tapes of an appropriate width of, for example, approximately 10 mm may be used as the carrier as arranged in parallel.

Also, it is feasible that, after a carded web is laminated, the carded web can be made wider by expanding the interval widths of the yarns or the tapes as the carrier.

The cotton yarns drawn from the cotton creed stand are introduced beneath the carded web in the above process, but the cotton yarns drawn from the cotton creed stand are introduced on the carded web, thereby to form a laminate to be led to the application unit.

(Manufacturing in Line of Coating Substrate with WJ Unit Incorporated)

Figure 4:
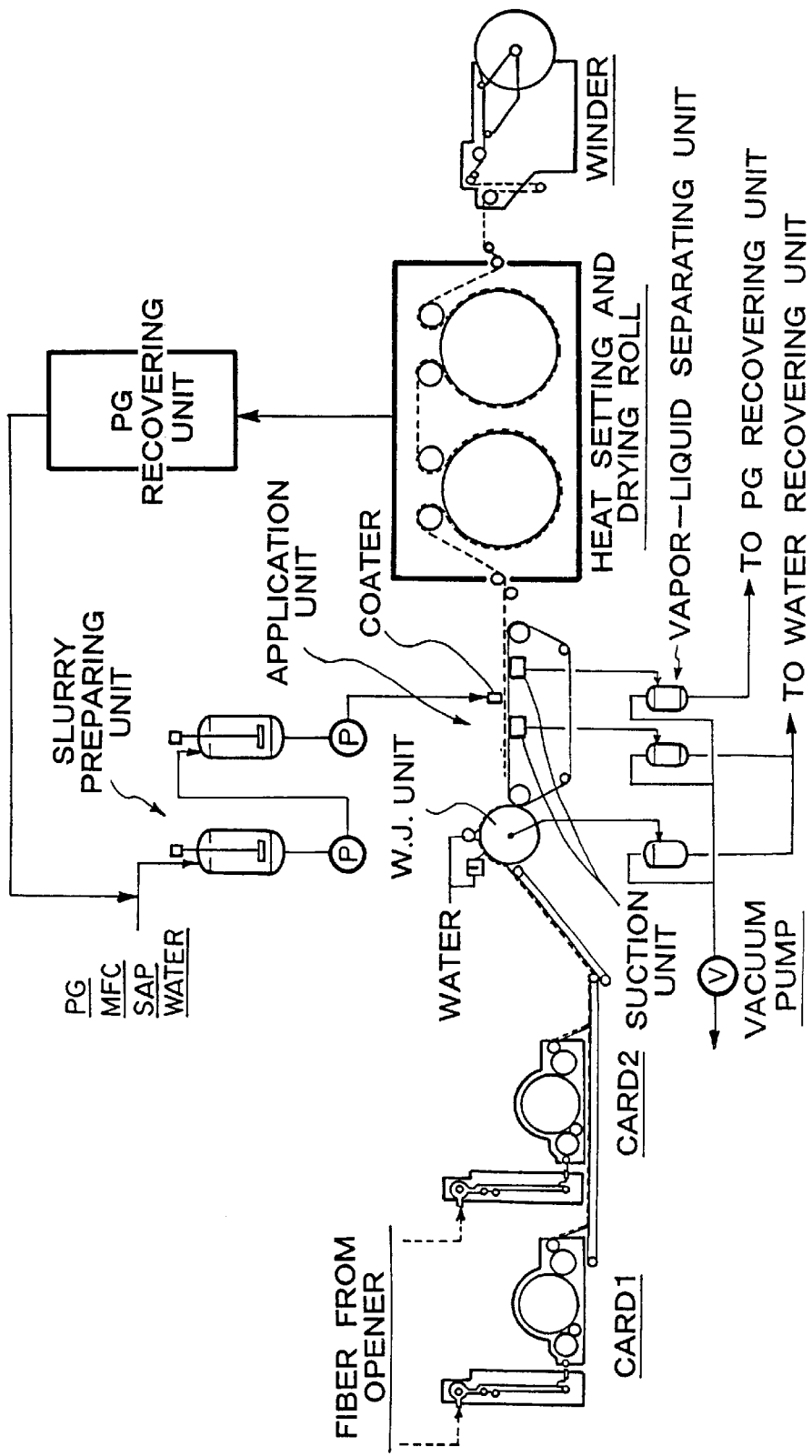
FIG. 4 is a schematic diagram showing a fourth manufacturing process based on a method of manufacturing a highly absorbent composite according to the present invention.

In the manufacturing process shown in FIG. 4, two cards are provided. As a first carded web as manufactured at a first card is transferred on a conveyor a second carded web as manufactured at a second card is laminated on the first carded web, and the laminated two-layer carded web is fed to a water jet (WJ) unit via a conveyor.

The WJ unit is so configured that a carded web as transferred on the peripheral surface of a roll with its peripheral wall constructed of a perforated plate is coated first with water to make it wet and a jet stream is applied on the carded web to entangle the constituent fibers of the carded web with each other. This water stream entangling is to give a shape retention of an extent not causing any trouble in the subsequent transferring and handling operations, so that it may be relatively light. Any excess liquid coming out of the WJ unit is suctioned at a suction unit similar to the suction unit at a subsequent application unit and discharged out of the system by means of a gas-liquid separation unit.

Any other configuration and operations are the same as those of the manufacturing process of FIG. 1, only except a precoat is omitted for coating water.

A preferable example of the composition of the first carded web is PET (5d)/Melty (2d), 20 g/m², and a preferable example of the composition of the second carded web is rayon (1d), 20 g/m².

An advantage of this manufacturing process is that, since water used after the water entangling treatment at the WJ unit can be handled as it is in a precoated condition, a precoat is not required and that naturally a separate step of removing such water is not required to be provided.

(Manufacturing in Line of Coating Substrate with Foaming Wet Laid Process Incorporated)

Figure 5:
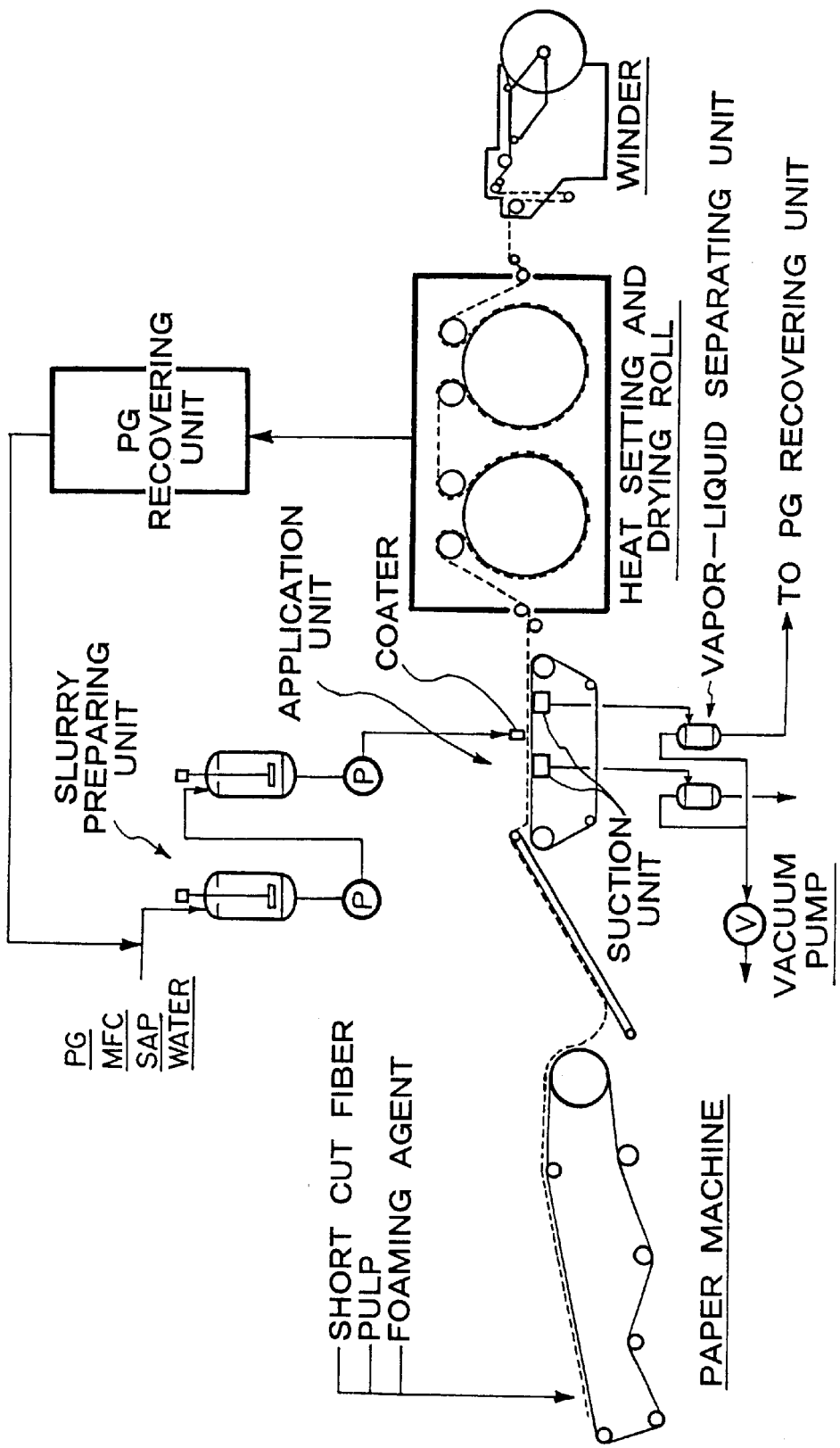
FIG. 5 is a schematic diagram showing a fifth manufacturing process based on a method of manufacturing a highly absorbent composite according to the present invention.

The foaming process shown in FIG. 5 is a processing which a foaming-agent and an activator as required are added to a mixed slurry of short cut fibers (for example, PE/PET (2d×5 mm)) and pulp to foam the slurry and the foamed mixture is formed into a wet web on a sheet on a plastic conveyor of paper making.

The wet web as obtained in the foaming wet laid process is sent to an application unit via a conveyor and given slurry there. In this case, too, the wet web is a water precoated web as it were and as such the slurry can be applied with no precoat applied.

All the subsequent parts of the manufacturing process are the same as those shown in FIG. 1. In this case, too, a separate step of removing used water is not required.

(Manufacturing in Line of Coating Substrate with Air Laid Former Incorporated)

Figure 6:
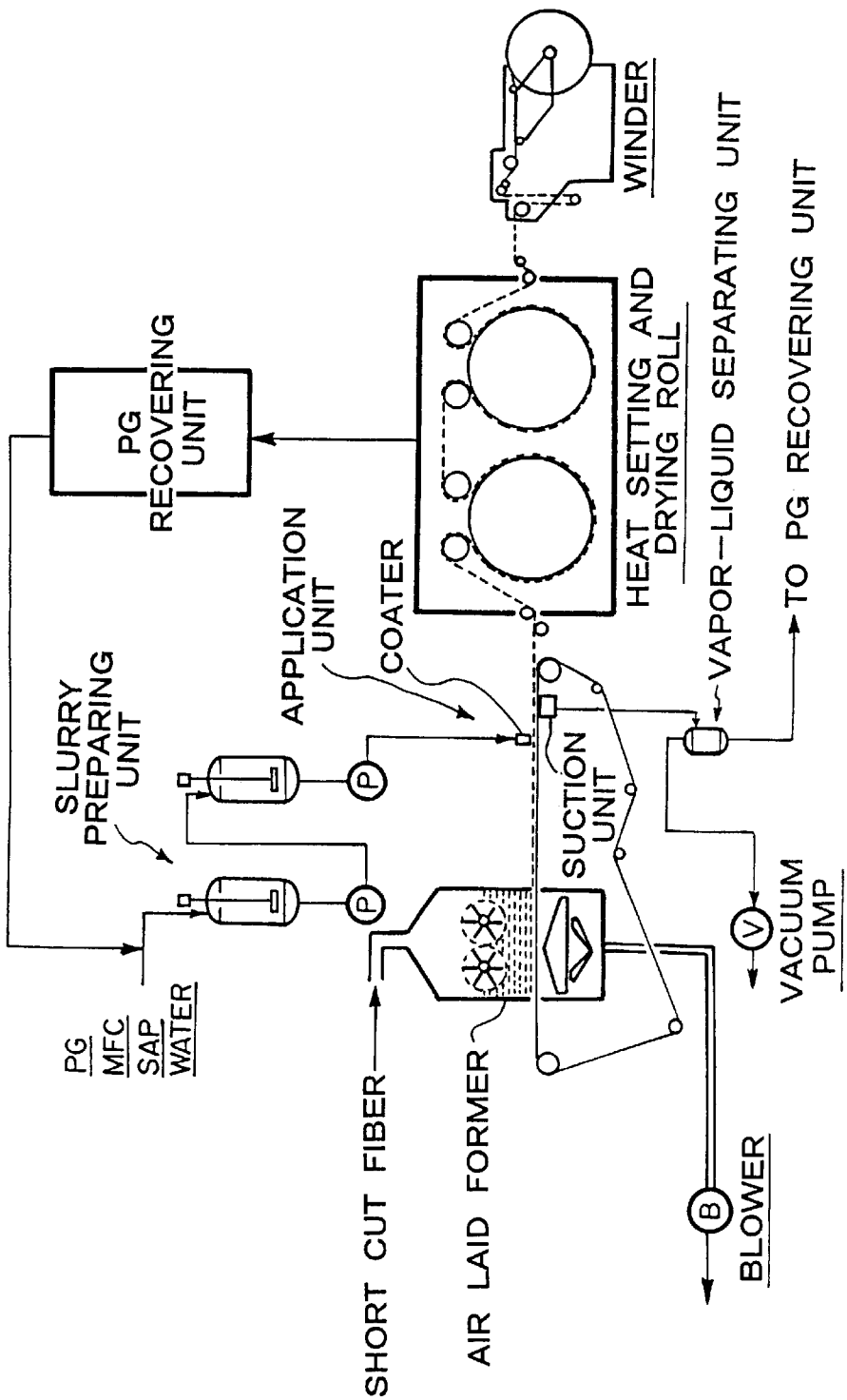
FIG. 6 is a schematic diagram showing a sixth manufacturing process based on a method of manufacturing a highly absorbent composite according to the present invention.

An air laid former is a device for making a fiber mat of air laid short cut fibers such as PE/PET and PP/PE, and in the manufacturing process shown in FIG. 6 an air laid former is provided in the upstream side and an application unit is provided in the downstream side of the belt running direction in a planate treatment region constructed on an endless belt.

Slurry is applied on the surface of an unbonded web of air laid mat form in the application unit, and then the web is led to a heat treatment and drying roll just as in the above-described processes. All the subsequent configurations and operations are the same as those in FIGS. 1 to 5 above.

Interlayer separation is likely to take place in an unbonded web of air laid mat form, so it may be sometimes preferable to have and use a carrier arranged in parallel such as tapes of spun yarn or spun laced non-woven fabric just as in FIG. 3 above.

(Manufacturing in Line of Substrate to be Obtained with a Bonded Spun Bond and an Unbonded Spun Bond as Combined)

Figure 7:
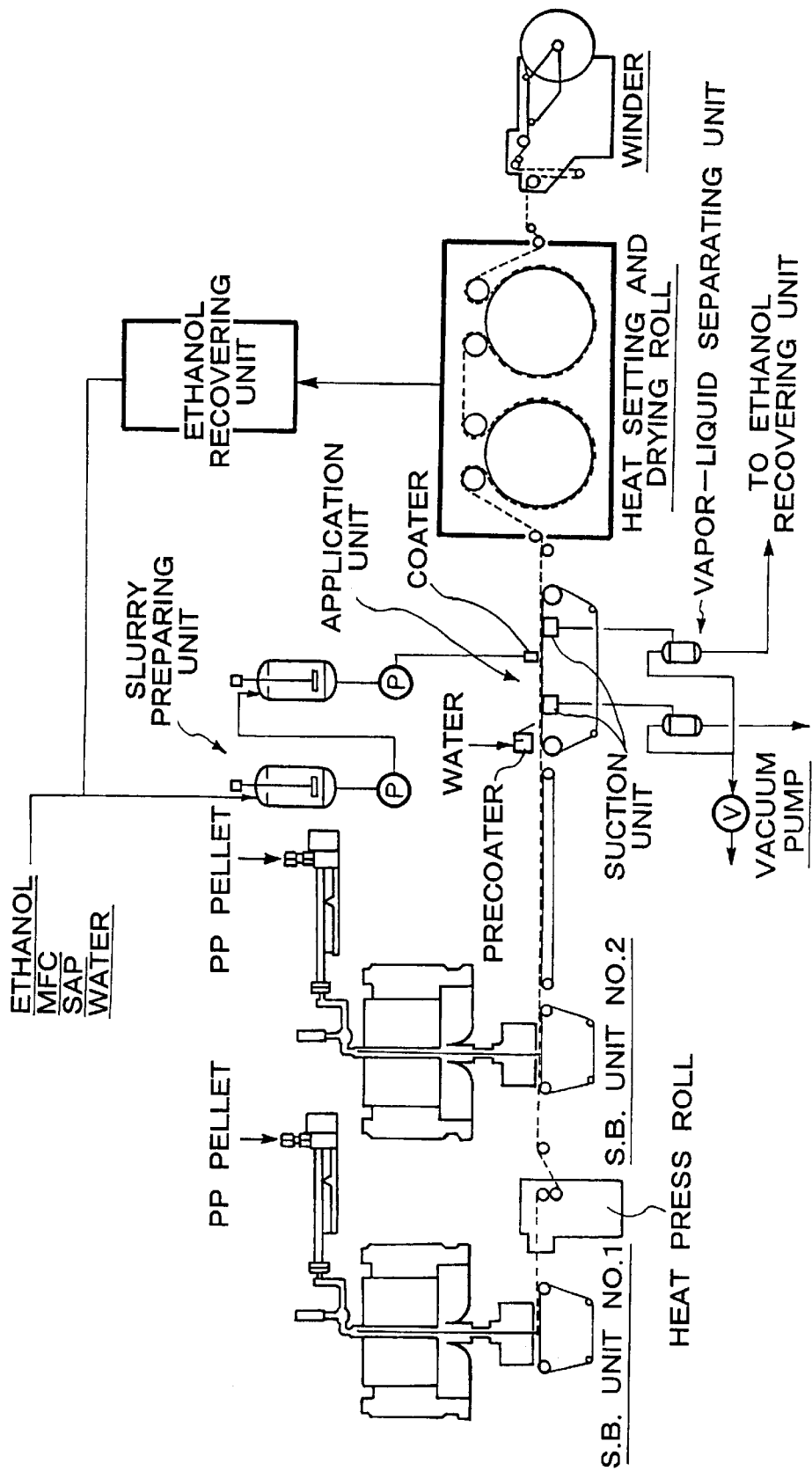
FIG. 7 is a schematic diagram showing a seventh manufacturing process based on a method of manufacturing a highly absorbent composite according to the present invention.

FIG. 7 shows an example of a process for manufacturing a non-woven fabric substrate with a bonded spun bond and an unbonded spun bond as combined, which is an embodiment of the present invention for manufacturing a highly absorbent composite sheet. The substrate is made by combining a relatively dense layer consisting of fine denier fibers (preferably 2d or finer) which is a first spun bond layer and a relatively bulky layer consisting of coarse denier fibers (preferably 3d or coarser), and it is preferable to bond the first layer relatively strongly and the second layer relatively weakly in combining the first and the second layer. Therefore, in this embodiment of the present invention, an unbonded second web is folded on a web bonded in which the first layer is bonded on a heat embossing roll, and the folded webs are precoated with a water dispersion liquid containing MFC for imparting a hydrophilic property and led to the application unit.

UTILIZATION OF THE PRESENT INVENTION IN INDUSTRY

As explained in the foregoing, according to the present invention in the process of manufacturing non-woven fabrics the manufacturing of non-woven fabrics and carrying and holding SAP in the non-woven fabrics can be fulfilled almost concurrently, and furthermore, neither powder dust is generated nor SAP particles move in an absorbent member, and with the fundamental properties of a non-woven fabric as a substrate sufficiently maintained, a highly absorbent composite sheet is obtained having all three functions of a supporter, holding and fixing SAP and permeation and dispersion.

Such highly absorbent composite sheet can be advantageously used as an absorbent member of an absorbent article such as a baby diaper, an adult incontinence diaper, female hygiene product, sanitary napkin, a blood absorbent and mother's milk pad.

In addition, no web of a bulky structure, which has spaces among its constituent fibers, needs to be transported, the transportation and handling costs are much reduced and thus the highly absorbent composite sheet according to the present invention has outstanding benefits in terms of the costs.

What is claimed is:

1. A method of manufacturing a highly absorbent composite sheet mainly consisting of a fibrous web substrate, a super absorbent resin, and a bonding agent to bond said substrate and said super absorbent resin, wherein (a) said fibrous web substrate is an unbonded web having substantially no bonding portions among its constituent fibers, (b)

said super absorbent resin and said bonding agent are dispersed in a liquid mixture containing an aqueous medium which does not swell said absorbent resin, (c) the resulting dispersion mixture is added to said unbonded fibrous web substrate to obtain a composite web, and (d) a liquid component is removed from said composite web, whereby fixing of said super absorbent resin onto said fibrous web substrate is effected simultaneously with bonding of constituent webs of said fibrous web substrate with one another.

2. The method of manufacturing a highly absorbent composite sheet of claim 1, wherein said unbonded web is a carded web or a laminate of the carded web.

3. The method of manufacturing a highly absorbent composite sheet of claim 1, wherein said unbonded web consists of a carded web and a carrier for guiding the carded web.

4. The method of manufacturing a highly absorbent composite sheet of claim 1, wherein said unbonded web is an air laid web obtained by an air laid process or a laminate of the air laid web.

5. The method of manufacturing a highly absorbent composite sheet of claim 1, wherein said unbonded web is a spun bonded web or a laminated of the spun bonded web.

6. The method of manufacturing a highly absorbent composite sheet of claim 1, wherein an aqueous medium consisting of water or a water miscible medium solution is preliminarily applied to the unbonded web obtained in a dry state.

7. The method of manufacturing a highly absorbent composite sheet of claim 1, wherein said unbonded web is an aqueous web obtained by a wet-laid forming method or a laminate of the aqueous web.

8. The method of manufacturing a highly absorbent composite sheet of claim 1, wherein said unbonded web is an aqueous web obtained only by pretreating the unbonded web in a pressurized water stream or a laminate of the aqueous web.

9. The method of manufacturing a highly absorbent composite sheet of claim 1, wherein a fiber component constituting said unbonded web consists of a combination of thermally fusible fibers and synthetic fibers.

10. The method of manufacturing a highly absorbent composite sheet of claim 1, wherein a fiber component constituting said unbonded web consists of a first fibrous layer mainly consisting of 2 denier or coarser and 10 denier or finer hydrophobic fibers and a second fibrous layer mainly consisting of 3 denier or finer hydrophilic fibers.

11. The method of manufacturing a highly absorbent composite sheet of claim 1, wherein said unbonded web consists of fibers obtained by opening wood pulp and thermally fusible fibers which are 20 mm long or shorter.

12. The method of manufacturing a highly absorbent composite sheet of claim 1, wherein said liquid mixture is a slurry made by dispersing super absorbent resin particles in a solution in which 1% or less of polyethylene oxide of high degree of polymerization of 100,000 or more in molecular weight is dispersed.

13. The method of manufacturing a highly absorbent composite sheet of claim 1, wherein said liquid mixture is a slurry made by dispersing super absorbent resin particles in an aqueous emulsion of ethylene-vinyl acetate copolymer.

14. The method of manufacturing a highly absorbent composite sheet of claim 1, wherein said liquid mixture system is an aqueous slurry of a super absorbent resin containing a solvent obtained by inverse phase suspension polymerization.

15. The method of manufacturing a highly absorbent composite sheet of claim 1, wherein said liquid mixture is made fluid by diluting an aggregated gel of a super absorbent resin obtained through an aqueous solution polymerization with polypropylene glycol.

16. The method of manufacturing a highly absorbent composite sheet of claim 1, wherein said liquid mixture is a slurry made by dispersing super absorbent resin particles in an aqueous dispersion liquid of microfibrillated fibrils having a hydrating property.

17. The method of manufacturing a highly absorbent composite sheet of claim 12, wherein microfibrillated fibrils having a hydrating property are added to said liquid mixture.

18. The method of manufacturing a highly absorbent composite sheet of claim 13, wherein microfibrillated fibrils having a hydrating property are added to said liquid mixture.

19. The method of manufacturing a highly absorbent composite sheet of claim 14, wherein microfibrillated fibrils having a hydrating property are added to said liquid mixture system.

20. The method of manufacturing a highly absorbent composite sheet of claim 15, wherein microfibrillated fibrils having a hydrating property are added to said liquid mixture system.

21. The method of manufacturing a highly absorbent composite sheet of claim 6, wherein microfibrillated fibrils having a hydrating property are added to said pretreatment liquid.

22. The method of manufacturing a highly absorbent composite sheet of claim 1, wherein said super absorbent resin is so surface cross-linked that it has 25 ml/g or higher AUL (absorbance under load) under 20 $g/cm^2$ in a saline water containing 0.9% salt.

23. The method of manufacturing a highly absorbent composite sheet of claim 1, wherein said super absorbent resin is a polymer of an amino acid type having as a platform asparaginic acid having a biodegrading property as not surface cross-linked.

24. The method of manufacturing a highly absorbent composite sheet of claim 1, wherein said super absorbent resin is a polyacrylic acid type polymer with surface cross-linking treatment not applied on.

25. The method of manufacturing a highly absorbent composite sheet of claim 16, wherein said microfibrillated fibrils having a hydrating property are microfibrillated cellulose or bacterium cellulose consisting of cellulose.

26. The method of manufacturing a highly absorbent composite sheet of claim 16, wherein as said microfibrillated fibrils having a hydrating property microfibrillated cellulose fibers are used and the microfibrillated cellulose fibers are uniformly dispersed in a mixed solvent of water and propylene glycol at a concentration of 1.5% to 0.2% and a slurry made by dispersing super absorbent resin particles at a concentration of 5% to 50% in the dispersion liquid is used.

27. The method of manufacturing a highly absorbent composite sheet of claim 16, wherein as said microfibrillated fibrils having a hydrating property microfibrillated cellulose fibers are used and the microfibrillated cellulose fibers are uniformly dispersed in a mixed solvent of water and ethyl alcohol at a concentration of 1.5% to 0.2% and a slurry made by dispersing super absorbent resin particles at a concentration of 5% to 50% in the dispersion liquid is used.

28. The method of manufacturing a highly absorbent composite sheet of claim 16, wherein as said microfibrillated fibrils having a hydrating property microfibrillated cellulose fibers are used and the microfibrillated cellulose fibers are uniformly dispersed in a three component mixed solvent of water, ethanol and propylene glycol at a concentration of 1.5% to 0.2% and a slurry made by dispersing super absorbent resin particles at a concentration of 5% to 50% in the dispersion liquid is used.

* * * * *